(12) United States Patent
Thennati et al.

(10) Patent No.: US 9,707,182 B2
(45) Date of Patent: Jul. 18, 2017

(54) ORAL PHARMACEUTICAL DOSAGE FORMS OF BUDESONIDE

(71) Applicant: Sun Pharmaceutical Industries Ltd., Mumbai (IN)

(72) Inventors: Rajamannar Thennati, Baroda (IN); Shirish Kulkarni, Baroda (IN); Amol Kulkarni, Baroda (IN); Vimal Kaneria, Bopal (IN); Mukesh Sharma, Baroda (IN)

(73) Assignee: Sun Pharmaceutical Industries LTD., Maharashtra (IN)

(*) Notice: Subject to any disclaimer, the term of this patent is extended or adjusted under 35 U.S.C. 154(b) by 0 days.

(21) Appl. No.: 15/261,420

(22) Filed: Sep. 9, 2016

(65) Prior Publication Data

US 2017/0071863 A1 Mar. 16, 2017

(30) Foreign Application Priority Data

Sep. 11, 2015 (IN) .......................... 3498/MUM/2015

(51) Int. Cl.
*A61K 9/48* (2006.01)
*A61K 31/58* (2006.01)
*A61K 9/50* (2006.01)

(52) U.S. Cl.
CPC .......... *A61K 9/4816* (2013.01); *A61K 9/4808* (2013.01); *A61K 9/4858* (2013.01); *A61K 9/4866* (2013.01); *A61K 9/4891* (2013.01); *A61K 9/5078* (2013.01); *A61K 31/58* (2013.01); *A61K 9/5015* (2013.01); *A61K 9/5026* (2013.01); *A61K 9/5047* (2013.01)

(58) Field of Classification Search
None
See application file for complete search history.

(56) References Cited

U.S. PATENT DOCUMENTS

| | | | |
|---|---|---|---|
| 5,643,602 A * | 7/1997 | Ulmius | A61K 31/58 424/461 |
| 5,932,249 A | 8/1999 | Gruber et al. | |
| 6,214,378 B1 | 4/2001 | Tanida et al. | |
| 6,413,494 B1 | 7/2002 | Lee et al. | |
| 6,531,150 B1 * | 3/2003 | Sunohara | A61K 9/4891 424/451 |
| 8,491,932 B2 | 7/2013 | Watts et al. | |
| 8,895,064 B2 | 11/2014 | Villa et al. | |
| 8,945,616 B2 | 2/2015 | Murty et al. | |
| 2005/0089571 A1 | 4/2005 | Beckert et al. | |
| 2010/0209501 A1 * | 8/2010 | Murty | A61K 9/2072 424/457 |
| 2010/0209520 A1 | 8/2010 | Kubo | |
| 2012/0021052 A1 * | 1/2012 | Villa | A61K 9/0053 424/457 |
| 2015/0118296 A1 | 4/2015 | Kulkarni et al. | |

FOREIGN PATENT DOCUMENTS

WO    WO2015071812    5/2015

OTHER PUBLICATIONS

United States District Court for the District of Delaware. *Astrazeneca LP et al.* v. *Mylan Pharmaceuticals Inc.* C.A. No. 08-453-GMS, 13 pages, decided Jun. 23, 2011. Downloaded from http://www.ded.uscourts.gov/sites/default/files/opinions/gms/2011/june/08-453.pdf on Oct. 24, 2016.*
FDA Center for Drug Evaluation and Research. ANDA 090410. Downloaded from http://www.accessdata.fda.gov/drugsatfda_docs/anda/2010/090410Orig1s000BioeqR.pdf on Oct. 24, 2016, 69 sheets with unusual page numbering.*
"Package Insert for Entocort EC (budesonide) capsules" Dec. 2011.
"Package Insert for Budenofalk 9 mg gastro-resistant granules" Dec. 2010.
"Package Insert for UCERIS (budesonide) extended release tablets, for oral use" Jan. 2013.

* cited by examiner

*Primary Examiner* — Isaac Shomer

(74) *Attorney, Agent, or Firm* — Davidson, Davidson & Kappel, LLC

(57) ABSTRACT

The present invention relates to novel oral sustained release pharmaceutical dosage forms for delivery of budesonide to the lower gastrointestinal tract for the treatment of Crohn's disease.

15 Claims, No Drawings

ORAL PHARMACEUTICAL DOSAGE FORMS OF BUDESONIDE

FIELD OF THE INVENTION

The invention relates to novel oral sustained release pharmaceutical dosage forms for delivery of budesonide to the lower gastrointestinal tract. The present invention also relates to methods of making the same. In particular, the invention relates to pharmaceutical dosage forms of budesonide for delivery to the lower gastrointestinal tract for the treatment of Crohn's disease as well as for the maintenance of clinical remission of mild to moderate Crohn's disease involving the ileum and/or the ascending colon

BACKGROUND OF THE INVENTION

Budesonide is a synthetic corticosteroid which has been effective for the treatment of inflammatory diseases of the gastrointestinal tract such as Crohn's disease and ulcerative colitis. The chemical name of budesonide is The chemical name for budesonide is 16,17-(butylidenebis(oxy))-11,21-dihydroxy-, (11-β,16-α)-pregna-1,4-diene-3,20-dione, and its chemical structure is shown as below:

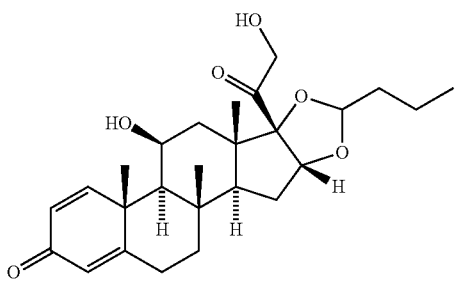

Budesonide is commercially available in United States as a capsule composition ENTOCORT® EC for the treatment of mild to moderate active Crohn's disease and the maintenance of clinical remission of mild to moderate Crohn's disease involving the ileum and/or the ascending colon. ENTOCORT® EC is available as a 3 mg capsule and the recommended dosing is 9 mg orally taken once daily i.e 3 capsules taken orally at a time. Treatment of inflammatory diseases of gastrointestinal tract requires targeted drug delivery to the small intestine and colon.

U.S. Pat. No. 5,643,602 discloses a composition comprising a non-pareil seed coated with first layer of a glucocorticoid and a film forming water insoluble polymer or water soluble polymer. Compositions used to layer the glucocorticoid on the non-pareil seed are known to form a film coating because the proportion of the film forming polymer in such composition is high. This layer is further coated with anionic carboxylic polymer like acrylic acid polymers. The patent particularly exemplifies budesonide in the working examples and prepares sustained release capsules comprising 0.5 to 2 mg of budesonide.

The present inventors have found that release of water insoluble drug such as budesonide can be controlled even when instead of forming a film coating such as that disclosed in U.S. Pat. No. 5,643,602, one forms a matrix layer containing a sugar and water insoluble polymer in a ratio greater than 3:1. This finding was surprising in view of the water solubility of the sugar which was the major component of the novel matrix layer. The sugar matrix layering composition was found useful in layering a higher load of budesonide particles per inert core and thus reduced the weight of the composition that needed to be filled into capsule. Even 9 mg budesonide could be formulated as a sustained release coating over the inert cores and the coated cores conveniently filled into single size 1 capsule. The present invention is also useful in providing a single unit dosage form such as one capsule containing the daily dose of budesonide in contrast to the marketed product Entocort® EC where 2 or 3 capsules may be required to be ingested by the patient.

SUMMARY OF THE INVENTION

The present invention provides a sustained release pharmaceutical dosage form comprising:
   a) an inert core,
   b) a first sustained release sugar matrix layer surrounding the inert core, the sugar matrix layer comprising budesonide, a water insoluble polymer and sugar, wherein the ratio of sugar to water insoluble polymer is greater than 3:1; and
   c) a second delayed release film coating surrounding the sustained release sugar matrix layer.

The present invention also provides a sustained release dosage form in the form of a capsule, sachet or pouch comprising 9 mg of budesonide per capsule, sachet or pouch wherein, the sustained release pharmaceutical dosage form when tested for dissolution in a USP Apparatus II at 75 rpm in 1000 ml of 0.1 N HCl for 2 hours followed by a change to pH 5.5 buffer, exhibits the following dissolution profile:
   a) less than 5% of total budesonide is released after 2 hours;
   b) from about 5% to about 15% of total budesonide is released after 3 hours;
   c) from about 15% to about 20% of total budesonide is released after 4 hours;
   d) from about 30% to about 40% of total budesonide is released after 6 hours;
   e) from about 40% to about 50% of total budesonide is released after 8 hours; and
   f) not less than 50% of total budesonide is released after 10 hours and,
when tested for dissolution in a USP Apparatus II at 75 rpm in 1000 ml of 0.1 N HCl for 2 hours followed by a change to pH 7.5 buffer, exhibits the following dissolution profile:
   a) less than 5% of total budesonide is released after 2 hours;
   b) from about 30% to about 50% of total budesonide is released after 3 hours;
   c) from about 40% to about 60% of total budesonide is released after 4 hours;
   d) from about 65% to about 85% of total budesonide is released after 6 hours; and
   e) not less than 80% of total budesonide is released after 8 hours.

DETAILED DESCRIPTION OF THE INVENTION

The release budesonide from the formulations of the invention is particularly adapted for the treatment of Crohn's disease and for the maintenance of clinical remission of mild to moderate Crohn's disease involving the ileum and/or the ascending colon.

The term "inert core" herein refers to a core that is pharmacologically inert in that it does not comprise a drug.

The inert core of the present sustained release pharmaceutical dosage form consists of a non-pareil seed. In a preferred embodiment, the non-pareil seeds are symmetric round shape e.g spherical or oval cores. In a particular embodiment, the non-pareil seeds are sugar spheres. The size of the sugar spheres is below 750 µm, preferably 25-30 mesh size (i.e 710 µm –600 µm).

The present inventors have surprisingly found that a first sustained release sugar matrix layer surrounding the inert core comprising sugar and water insoluble polymer in a ratio greater than 3:1 forms a sustained release matrix layer for the release of budesonide. As used herein the term sugar is intended to mean sucrose. The layer can be characterized as a "matrix" rather than a "film" because the matrix layering composition is incapable of forming a film when tested for the same by known conventional method of film casting. The first sustained release sugar matrix layer surrounding the inert core comprises budesonide, a water insoluble polymer and sugar. The amount of sugar in the first sustained release sugar matrix layer is from about 50% to about 80% of the total weight of sugar matrix layer. In a preferred embodiment, the amount of sugar in the first sustained release sugar matrix layer is about 63% of the total weight of sugar matrix layer.

The amount of water insoluble polymer in the first sustained release sugar matrix layer is from about 5% to about 25% of the total weight of sugar matrix layer. Preferably, the amount of water insoluble polymer in the sugar matrix layer is from about 5% to about 15% of the total weight of sugar matrix layer, preferably, about 12% of the total weight of sugar matrix layer. The ratio of sugar to water insoluble polymer in the first sustained release sugar matrix layer is greater than 3:1, preferably in the range of about 3:1 to about 6:1. Most preferably the ratio of sugar to water insoluble polymer in the first sustained release sugar matrix layer is about 5:1.

Water insoluble polymer herein is selected from ethyl cellulose, polyvinyl acetate, polyvinyl pyrrolidone, polyacrylate. Preferably, the water insoluble polymer is ethyl cellulose. Alternatively ethyl cellulose may be used as Aquacoat® ECD, Surelease® or Ethocel®. Budesonide is incorporated in the sustained release sugar matrix layering composition preferably in the form of micronized budesonide. The micronized budesonide preferably has a particle size in the range of about 0.2 µm to about 20 µm, preferably about 0.5 to about 10 µm. The amount of budesonide in the sustained release pharmaceutical dosage form is in the range of about 6 mg to about 9 mg. In a preferred embodiment, the amount of in the sustained release pharmaceutical dosage form is 6 mg. In another preferred embodiment, the amount of budesonide in the in the sustained release pharmaceutical dosage form is 9 mg. Budesonide is incorporated in the sustained release sugar matrix layer in an amount from about 10% to about 30%, preferably from about 15% to about 25% of the total weight of sugar matrix layer. Budesonide is present in an amount from about 1.5% to about 3.5% of the total weight of sustained release pharmaceutical dosage form. The sustained release pharmaceutical dosage form of the present invention also comprises a delayed release film coating which surrounds the sustained release sugar matrix layer. The delayed release film coating comprises polymers that are soluble at pH higher than about 5, for eg. acrylic acid polymers, hydroxypropylmethylcellulose phthalate (HPMC-P), HPMC acetate succinate (HPMC-AS) or mixtures thereof. Preferably, the delayed release film coating comprises copolymers of acrylic acid and methacrylic acid esters. More preferably, the copolymers of acrylic acid and methacrylic acid esters are Eudragit® L 30 D-55, Eudragit® L 100-55, Eudragit® L 100, Eudragit® L 12,5, Eudragit® S 100, Eudragit® S 12,5, Eudragit® FS 30 D. In a particularly preferred embodiment, the delayed release film coating comprises copolymers of acrylic acid and methacrylic acid ester is a 1:1 copolymer of methacrylic acid and ethyl acrylate, such as Eudragit® L 30 D-55. The amount of copolymers of acrylic acid and methacrylic acid esters in the delayed release film coating is from about 50% to about 70% of the total weight of delayed release film coating. In a preferred embodiment, the amount of methacrylic acid-ethyl acrylate copolymer 1:1 in the delayed release film coating is about 62% of the total weight of delayed release film coating.

The first sustained release sugar matrix layer as well as the second delayed release film coating may further comprise a plasticizer. Suitable plasticizers for use in the present sustained release pharmaceutical dosage form may be selected from the group consisting of acetyl tributyl citrate, triethyl citrate, dibutyl sebacate and tri-n-butyl citrate or mixtures thereof. Plasticizers may be present in an amount from about 5% to about 10% of the total weight of sustained release pharmaceutical dosage form. Preferably, the plasticizer may be present in an amount from about 7% w/w to about 15% w/w of water insoluble polymer in the sugar matrix layer and 5% w/w to 15% w/w of the polymers in the delayed release film coating.

The coated cores of the present invention may further comprise other excipients but are not limited to stabilizing agents and/or wetting agents such as polysorbate 80 sodium lauryl sulfate, cetyl alcohol, ammonium oleate, antifoaming agents such as simethicone emulsion, lubricants such as magnesium stearate, glyceryl monostearate or stearic acid and glidant such as colloidal silicon dioxide and talc.

The sustained release pharmaceutical dosage form of budesonide of the present invention may be a capsule, sachet or a pouch. In a preferred embodiment, the pharmaceutical dosage form of budesonide of the present invention is a capsule. Alternatively, coated cores may be compressed into a tablet.

The sustained release pharmaceutical dosage form of the present invention releases budesonide gradually over the intestine beginning from small intestine to large intestine. The sustained release pharmaceutical dosage form of the present invention when tested for dissolution in a USP Apparatus II at 75 rpm in 1000 ml of 0.1 N HCl for 2 hours followed by a change to pH 5.5 buffer, exhibits the following dissolution—
  a) less than 5% of total budesonide is released after 2 hours;
  b) from about 5% to about 15% of total budesonide is released after 3 hours;
  c) from about 15% to about 20% of total budesonide is released after 4 hours;
  d) from about 30% to about 40% of total budesonide is released after 6 hours;
  e) from about 40% to about 50% of total budesonide is released after 8 hours; and
  f) not less than 50% of total budesonide is released after 10 hours.

The sustained release pharmaceutical dosage form of the present invention when tested for dissolution in a USP Apparatus II at 75 rpm in 1000 ml of 0.1N HCl for 2 hours followed by a change to pH 7.5 buffer, exhibits the following dissolution—
  a) less than 5% of total budesonide is released after 2 hours;

b) from about 30% to about 50% of total budesonide is released after 3 hours;
c) from about 40% to about 60% of total budesonide is released after 4 hours;
d) from about 65% to about 85% of total budesonide is released after 6 hours; and
e) not less than 80% of total budesonide is released after 8 hours.

The sustained release pharmaceutical dosage form of the present invention is useful in the treatment of Crohn's disease and maintenance of clinical remission of mild to moderate Crohn's disease involving the ileum and/or the ascending colon.

DETAILED DESCRIPTION OF EMBODIMENTS

The compositions of the present invention example are described in detail. The compositions of the present invention may be understood by the following illustrative example but are by no means limited by the specific example.

EXAMPLE 1

Inert Cores:

300 Kg of inert cores, preferably of symmetric round shape, e.g. spherical or oval cores for example sugar spheres in the size range from about 600 μm to about 710 μm (#25-#30) are loaded into the product container of a fluid bed processor.

Preparation of the Sugar Matrix Layer Composition:

The sugar matrix layering composition may be as follows—

| S. No | Ingredient | Kg |
|---|---|---|
| 1. | Budesonide | 9.0 |
| 2. | Ethyl cellulose* | 4.6 to 5.6 |
| 3. | Sodium Lauryl sulfate* | 0.15 to 0.35 |
| 4. | Cetyl alcohol* | 0.3 to 0.7 |
| 5. | Sucrose | 26.0 |
| 6. | Acetyl Tributyl Citrate | 0.4 |
| 7. | Polysorbate 80 | 0.1 |
| 8. | Water | 221.0 |

*were added in this example in form of 19 kg of Aquacoat ® ECD.

Acetyltributyl citrate is added to Aquacoat® ECD. Sucrose is dissolved in water and the above Aquacoat dispersion is added to this sucrose solution. Polysorbate 80 in water is added to the above dispersion under stirring. To this budesonide is added and stirred. This dispersion is passed thorough ASTM 80# sieve (180μm) and remaining quantity of water is added.

Formation of the Sustained Release Sugar Matrix Layer

Sugar sphere are loaded to product container of fluid bed processor. The sugar matrix layering composition is sprayed on Sugar spheres at 39-43° C. at a rate of 3.0- 5.0 gm/min. The coated sugar spheres are dried after completion of spraying in fluid bed processor at 40-45° C. till the LOD is not more than 2.0% w/w. The coated sugar spheres are sift dried through ASTM 35# sieve (500 μm) to remove under size and through ASTM 20# sieve (850 μm) to remove oversize fraction.

Sustained release sugar matrix coated cores are blended with talc in suitable blender and cured in suitable tray dryer at 60±5° C. for 24 hours. Sugar matrix coated cores are cooled to room temperature and sifted through ASTM 35# sieve (500 μm).

The sugar matrix layering process results upon drying the formation of a sustained release sugar matrix layer having the following composition—

| S. No | Ingredient | % w/w |
|---|---|---|
| 1. | Budesonide | 21.76 |
| 2. | Ethyl cellulose | 12.33 |
| 3. | Sodium Lauryl sulfate | 0.6 |
| 4. | Cetyl alcohol | 1.2 |
| 5. | Sucrose | 62.88 |
| 6. | Acetyl Tributyl Citrate | 0.97 |
| 7. | Polysorbate 80 | 0.24 |

Preparation of Delayed Release Coating Suspension

| S. No | Ingredient | Kg |
|---|---|---|
| 1. | Methacrylic acid-ethyl acrylate copolymer 1:1 | 16.982 |
| 2. | Triethyl Citrate | 1.709 |
| 3. | Polysorbate80 | 0.097 |
| 4. | Purified Talc | 8.547 |
| 5. | Simethicone Emulsion 30% | 0.011 |
| 6. | Purified water | 70.0 |

For the delayed release coating methacrylic acid-ethyl acrylate copolymer 1:1 as Eudragit® L30 D55 is added to triethyl citrate and stirred to form Eudragit® dispersion. Polysorbate 80 aqueoud solution and simethicone emulsion are added to Eudragit dispersion with talc and purified water. This suspension is stirred and filtered through ASTM 60# sieve (250 μm).

Formation of Delayed Release Coating Layer

The sustained release sugar matrix coated cores are loaded into product container of fluid bed processor. The delayed release coating suspension are sprayed on to the sugar matrix coated cores at 28-32° C. at a rate of 3.0-5.0 gm/minute. After completion of spraying, the coated cores are dried at 30-40° C. till the LOD range: 0.25-2.0% w/w is achieved. The delayed release coated cores are sifted through ASTM 18# sieve (1 mm) to separate oversize fraction and through ASTM 35# sieve (500 μm) to separate undersize fraction. These delayed release coated cores are blended with talc and sifted through ASTM 16# sieve (1.18 mm) and collected.

These delayed release coated cores are then filled in hard gelatin capsules shells of Size "1" with per capsule 9 mg budesonide.

EXAMPLE 2

6 mg budesonide capsules are made using similar process as in Example 1 using excipients in a dose proportional to 9 mg strength and filled in Size "2" capsule shell.

EXAMLE 3

A 9 mg capsule of budesonide of Example 1 is placed in USP Apparatus II in a 1000mL of 0.1N HCl at 75RPM for 2 hours followed by a change in media to buffer of pH 5.5. Similarly, the 9 mg capsule of budesonide of Example 1 was tested for dissolution at pH7.5 wherein the capsule was placed in USP Apparatus II in a 1000 mL of 0.1 N HCl at 75 RPM for 2 hours followed by a change in media to buffer of pH7.5. For specified time periods fractions are collected and analyzed for budesonide. The percentage dissolution at each time point is calculated. The dissolution profiles at pH 5.5 and pH 7.5 are as shown in Table 1 and Table 2 respectively.

TABLE 1

Media: 0.1N HCl followed by pH 5.5, 1000 mL, USP-II, 75 RPM

| Time (Hours) | Example 1 |
|---|---|
| 2 | 1 |
| 3 | 8 |
| 4 | 17 |
| 6 | 31 |
| 8 | 44 |
| 10 | 54 |

TABLE 2

Media: 0.1N HCl followed by pH 7.5, 1000 mL, USP-II, 75 RPM

| Time (Hours) | Example 1 |
|---|---|
| 2 | 1 |
| 3 | 36 |
| 4 | 56 |
| 6 | 78 |
| 8 | 85 |

CONCLUSION

It will be readily apparent to one of ordinary skill in the relevant arts that other suitable modifications and adaptations to the methods and applications described herein are suitable and may be made without departing from the scope of the invention or any embodiment thereof. While the invention has been described in connection with certain embodiments, it is not intended to limit the invention to the particular forms set forth, but on the contrary, it is intended to cover such alternatives, modifications and equivalents as may be included within the spirit and scope of the invention as defined by the following claims.

We claim:

1. A sustained release pharmaceutical dosage form in the form of a capsule, sachet or pouch, comprising:
    a) an inert core,
    b) a first sustained release sugar matrix layer surrounding the inert core, the sugar matrix layer comprising budesonide, a water insoluble polymer and sugar, wherein the ratio of sugar to water insoluble polymer is greater than 3:1; and
    c) a second delayed release film coating surrounding the sustained release sugar matrix layer, wherein, the sustained release pharmaceutical dosage form when tested for dissolution in a USP Apparatus II at 75 rpm in 1000 ml of 0.1 N HCl for 2 hours followed by a change to pH 5.5 buffer, exhibits the following dissolution profile
        a) less than 5% of total budesonide is released after 2 hours;
        b) from about 5% to about 15% of total budesonide is released after 3 hours;
        c) from about 15% to about 20% of total budesonide is released after 4 hours;
        d) from about 30% to about 40% of total budesonide is released after 6 hours;
        e) from about 40% to about 50% of total budesonide is released after 8 hours;
        f) not less than 50% of total budesonide is released after 10 hours.

2. A sustained release pharmaceutical dosage form as in claim 1, wherein the water insoluble polymer is ethyl cellulose.

3. A sustained release pharmaceutical dosage form as in claim 1, wherein the sugar matrix layer comprises sugar in an amount from about 50 to about 80% of the total weight of sugar matrix layer.

4. A sustained release pharmaceutical dosage form as in claim 1, wherein the water insoluble polymer is present in an amount from about 5 to about 15% of the total weight of the sugar matrix layer.

5. A sustained release pharmaceutical dosage form of claim 1, wherein delayed release film coating comprises copolymers of acrylic acid and methacrylic acid esters.

6. A sustained release pharmaceutical dosage form of claim 1, wherein the amount of budesonide is in the range of from about 6mg to about 9mg.

7. A sustained release pharmaceutical dosage form of claim 1, wherein budesonide is present in an amount from about 15% to about 25% of the total weight of the sugar matrix layer.

8. A sustained release pharmaceutical dosage form of claim 1, wherein budesonide is present in an amount from about 1.5% to about 3.5% of the total weight of sustained release pharmaceutical dosage form.

9. A sustained release pharmaceutical dosage form of claim 1, for use in the treatment of Crohn's disease.

10. A sustained release pharmaceutical dosage form of claim 1, for use in the maintenance of clinical remission of mild to moderate Crohn's disease involving the ileum and/or the ascending colon.

11. A sustained release dosage form in the form of a capsule, sachet or pouch comprising:
    a) an inert core,
    b) a first sustained release sugar matrix layer surrounding the inert core, the sugar matrix layer comprising budesonide, a water insoluble polymer and sugar, wherein the ratio of sugar to water insoluble polymer is greater than 3:1; and
    c) a second delayed release film coating surrounding the sustained release sugar matrix layer, the sustained release pharmaceutical dosage form when tested for dissolution in a USP Apparatus II at 75 rpm in 1000 ml of 0.1 N HCl for 2 hours followed by a change to pH 5.5 buffer, exhibiting the following dissolution profile
        a) less than 5% of total budesonide is released after 2 hours;
        b) from about 5% to about 15% of total budesonide is released after 3 hours;
        c) from about 15% to about 20% of total budesonide is released after 4 hours;
        d) from about 30% to about 40% of total budesonide is released after 6 hours;
        e) from about 40% to about 50% of total budesonide is released after 8 hours;
        f) not less than 50% of total budesonide is released after 10 hours; and
        when tested for dissolution in a USP Apparatus II at 75 rpm in 1000 ml of 0.1 N HCl for 2 hours followed by a change to pH 7.5 buffer, exhibits the following dissolution profile,
        a) less than 5% of total budesonide is released after 2 hours;
        b) from about 30% to about 50% of total budesonide is released after 3 hours;
        c) from about 40% to about 60% of total budesonide is released after 4 hours;

d) from about 65% to about 85% of total budesonide is released after 6 hours;
e) not less than 80% of total budesonide is released after 8 hours.

12. A sustained release pharmaceutical dosage form of claim 11, for use in the treatment of Crohn's disease.

13. A sustained release pharmaceutical dosage form of claim 11, for use in the maintenance of clinical remission of mild to moderate Crohn's disease involving the ileum and/or the ascending colon.

14. A sustained release pharmaceutical dosage form as in claim 11, wherein the sugar matrix layer comprises sugar in an amount from about 50 to about 80% of the total weight of sugar matrix layer, and the water insoluble polymer is present in an amount from about 5 to about 15% of the total weight of the sugar matrix layer.

15. A sustained release pharmaceutical dosage form of claim 11, wherein delayed release film coating comprises copolymers of acrylic acid and methacrylic acid esters.

* * * * *